United States Patent
Cole et al.

(10) Patent No.: US 7,902,534 B2
(45) Date of Patent: Mar. 8, 2011

(54) CAVITY RING DOWN SYSTEM HAVING A COMMON INPUT/OUTPUT PORT

(75) Inventors: Barrett E. Cole, Bloomington, MN (US); James Allen Cox, New Brighton, MN (US); Terry Marta, White Bear Lake, MN (US); Carl Anderson, Prior Lake, MN (US); Rodney Thorland, Shoreview, MN (US)

(73) Assignee: Honeywell International Inc., Morristown, NJ (US)

( * ) Notice: Subject to any disclaimer, the term of this patent is extended or adjusted under 35 U.S.C. 154(b) by 204 days.

(21) Appl. No.: 12/233,396

(22) Filed: Sep. 18, 2008

(65) Prior Publication Data
US 2009/0185175 A1    Jul. 23, 2009

Related U.S. Application Data

(63) Continuation-in-part of application No. 11/633,872, filed on Dec. 4, 2006, now abandoned, which is a continuation-in-part of application No. 10/953,174, filed on Sep. 28, 2004, now Pat. No. 7,145,165.

(51) Int. Cl.
*G01J 1/00* (2006.01)

(52) U.S. Cl. .......... 250/573; 356/213; 313/506; 359/857

(58) Field of Classification Search .................. 250/573; 356/213; 313/506; 359/857
See application file for complete search history.

(56) References Cited

U.S. PATENT DOCUMENTS

| | | | |
|---|---|---|---|
| 4,233,568 A | 11/1980 | Hamerdinger et al. | |
| 4,612,647 A | 9/1986 | Norvell | |
| 4,614,961 A | 9/1986 | Khan et al. | |
| 4,870,224 A | 9/1989 | Smith et al. | |
| 4,973,131 A | 11/1990 | Carnes | |
| 5,022,745 A | 6/1991 | Zayhowski et al. | |
| 5,040,895 A | 8/1991 | Laurent et al. | |
| 5,135,304 A | 8/1992 | Miles et al. | |
| 5,146,465 A | 9/1992 | Khan et al. | |
| 5,278,435 A | 1/1994 | Van Hove et al. | |
| 5,311,280 A | 5/1994 | Koper et al. | |
| 5,408,319 A | 4/1995 | Halbout et al. | |

(Continued)

FOREIGN PATENT DOCUMENTS
DE        3311808        10/1984
(Continued)

OTHER PUBLICATIONS

Bernstein et al., "Development of a Miniature Silicon PhotoAcoustic Gas Sensor", Presented at Opto 96, Leipzig, Germany, 6 pages, Sep. 26-29, 1999.

(Continued)

*Primary Examiner* — Seung C Sohn
(74) *Attorney, Agent, or Firm* — Seager Tufte & Wickhem LLC

(57) ABSTRACT

A system having a multiple-mirror ring-down cavity with one mirror where light may be input into the cavity and light from the cavity may be detected. A valve may permit light to enter or not to enter the cavity. An amplifier may be connected to a detector for detecting light from the cavity. The amplifier may be off or set at a low gain when light is entering the cavity and be on at a medium or high gain at a time when light is not entering the cavity.

20 Claims, 15 Drawing Sheets

U.S. PATENT DOCUMENTS

| | | |
|---|---|---|
| 5,418,868 A | 5/1995 | Cohen et al. |
| 5,450,053 A | 9/1995 | Wood |
| 5,468,910 A | 11/1995 | Knapp et al. |
| 5,512,750 A | 4/1996 | Yanka et al. |
| 5,528,040 A | 6/1996 | Lemann |
| 5,550,373 A | 8/1996 | Cole et al. |
| 5,629,951 A | 5/1997 | Chang-Hasnain et al. |
| 5,677,538 A | 10/1997 | Moustakas et al. |
| 5,679,965 A | 10/1997 | Schetzina |
| 5,723,706 A | 3/1998 | Brasier et al. |
| 5,739,554 A | 4/1998 | Edmond et al. |
| 5,815,277 A | 9/1998 | Zare et al. |
| 5,832,017 A | 11/1998 | Ramdani et al. |
| 5,834,331 A | 11/1998 | Razeghi |
| 5,847,397 A | 12/1998 | Moustakas |
| 5,869,896 A | 2/1999 | Baker et al. |
| 5,900,650 A | 5/1999 | Nitta |
| 5,909,280 A | 6/1999 | Zavracky |
| 5,912,740 A | 6/1999 | Zare et al. |
| 5,915,051 A | 6/1999 | Damask et al. |
| 5,933,565 A | 8/1999 | Diebold |
| 5,960,025 A | 9/1999 | Thorland et al. |
| 6,040,895 A | 3/2000 | Haas |
| 6,080,988 A | 6/2000 | Ishizuya et al. |
| 6,084,682 A | 7/2000 | Zare et al. |
| 6,091,504 A | 7/2000 | Walker et al. |
| 6,115,122 A | 9/2000 | Bao et al. |
| 6,122,416 A | 9/2000 | Ooba et al. |
| 6,147,756 A | 11/2000 | Zavracky et al. |
| 6,208,798 B1 | 3/2001 | Morozov et al. |
| 6,287,940 B1 | 9/2001 | Cole et al. |
| 6,295,130 B1 | 9/2001 | Sun et al. |
| 6,296,779 B1 | 10/2001 | Clark et al. |
| 6,310,904 B1 | 10/2001 | Thorland et al. |
| 6,324,192 B1 | 11/2001 | Tayebati |
| 6,335,669 B1 | 1/2002 | Miyazaki et al. |
| 6,380,531 B1 | 4/2002 | Sugihwo et al. |
| 6,384,953 B1 | 5/2002 | Russell et al. |
| 6,404,648 B1 | 6/2002 | Slupe et al. |
| 6,406,578 B1 | 6/2002 | Schober et al. |
| 6,421,127 B1 | 7/2002 | McAndrew et al. |
| 6,438,149 B1 | 8/2002 | Tayebati et al. |
| 6,452,680 B1 | 9/2002 | Paldus et al. |
| 6,483,130 B1 | 11/2002 | Yang et al. |
| 6,492,726 B1 | 12/2002 | Quek et al. |
| 6,507,107 B2 | 1/2003 | Vaiyapuri |
| 6,545,739 B1 | 4/2003 | Matsumoto et al. |
| 6,583,917 B2 | 6/2003 | Melloni et al. |
| 6,584,126 B2 | 6/2003 | Wang et al. |
| 6,590,710 B2 | 7/2003 | Hara et al. |
| 6,594,059 B2 | 7/2003 | Flanders |
| 6,597,713 B2 | 7/2003 | Ouchi |
| 6,608,711 B2 | 8/2003 | Flanders et al. |
| 6,627,983 B2 | 9/2003 | Tu et al. |
| 6,658,034 B2 | 12/2003 | Garnache et al. |
| 6,670,599 B2 | 12/2003 | Wagner et al. |
| 6,728,286 B2 | 4/2004 | Thorland et al. |
| 6,816,636 B2 | 11/2004 | Cole et al. |
| 6,836,501 B2 | 12/2004 | Cox et al. |
| 6,879,014 B2 | 4/2005 | Wagner et al. |
| 6,985,281 B2 | 1/2006 | Wagner et al. |
| 7,002,697 B2 | 2/2006 | Domash et al. |
| 7,012,696 B2 | 3/2006 | Orr et al. |
| 7,015,457 B2 | 3/2006 | Cole et al. |
| 7,046,362 B2 | 5/2006 | Lehmann et al. |
| 7,049,004 B2 | 5/2006 | Domash et al. |
| 7,089,781 B2 | 8/2006 | Petrovic et al. |
| 7,106,763 B2 | 9/2006 | Tan et al. |
| 7,113,256 B2 | 9/2006 | Butler et al. |
| 7,145,165 B2 | 12/2006 | Cox et al. |
| 7,147,165 B2 | 12/2006 | Mongin et al. |
| 7,147,695 B2 | 12/2006 | Mitra |
| 7,221,827 B2 | 5/2007 | Domash et al. |
| 7,263,871 B2 | 9/2007 | Selker et al. |
| 7,304,799 B2 | 12/2007 | Ma et al. |
| 7,369,242 B2 | 5/2008 | Cole et al. |
| 7,649,189 B2 | 1/2010 | Cole |
| 2002/0191268 A1 | 12/2002 | Seeser et al. |
| 2004/0234198 A1 | 11/2004 | Wagner et al. |
| 2004/0255853 A1 | 12/2004 | Ma et al. |
| 2005/0030628 A1 | 2/2005 | Wagner et al. |
| 2005/0082480 A1 | 4/2005 | Wagner et al. |
| 2005/0105184 A1 | 5/2005 | Ma et al. |
| 2005/0254056 A1 | 11/2005 | Kachanov et al. |
| 2007/0133001 A1 | 6/2007 | Cox et al. |
| 2008/0151248 A1 | 6/2008 | Cole et al. |

FOREIGN PATENT DOCUMENTS

| | | |
|---|---|---|
| DE | 19635421 | 12/1997 |
| EP | 0177918 | 3/1991 |
| EP | 0667548 | 1/1995 |
| EP | 1069658 | 1/2001 |
| EP | 1061618 | 11/2007 |
| JP | 03252172 | 11/1991 |
| JP | 05095130 | 4/1993 |
| JP | 7288334 | 10/1995 |
| WO | 9326049 | 12/1993 |
| WO | 9942875 | 8/1999 |
| WO | 2004068123 | 8/2004 |

OTHER PUBLICATIONS

Brown, et al., "Visible-Blind UV Digital Camera Based on a 32*32 Array of GAN/AlGAN P-I-N Photodiodes", MRS Internet Journal of Nitride Semiconductor Research, vol. 451, pp. 1-10, Sep. 1999.

Campargue et al., "Measurement of SiH2 Density in a Discharge by Intracavity Laser Absorption Spectroscopy and CW Cavity Ring-Down Spectroscopy," Journal of Physics D. Applied Physics, vol. 31, No. 10 pp. 1168-1175, May 21, 1998.

Chitica et al., "Monolithic InP-Based Tunable Filter with 10-nm Bandwidth for Optical Data Interconnects in the 1550-nm Band," IEEE Photonics Technology Letters, vol. 11, No. 5, pp. 584-586, May 1999.

Chou et al., "Diode-Laser Measurements of He-, Ar-, and N2-Broadened HF Lineshapes in the First Overtone Band," Journal of Molecular Spectroscopy 196, pp. 70-76, 1999.

Chung et al., "Design and Fabrication of 10x10 Micro-Spatial Light Modulator Array for Phase and Amplitude Modulation," Sensors and Actuators, vol. 78, No. 1, pp. 63-70, Jan. 1999.

Cole et al., "Microscopic Spectroscopy of Optical MEMS Devices," Topic 2 (Materials and Technology), Honeywell Laboratories, 2 pages, on or Around Dec. 11, 2000.

Edwards, "Multiple-Traverse Absorption Cell Design," Journal of the Optical Society of America, vol. 51, No. 1, pp. 98-102, Jan. 1961.

Ferber et al., "A Miniature Silicon Photoacoustic Detector for Gas Monitoring Applications", presented at the MTEX International Conference on Sensors and Transducers, Birmingham, UK, 7 pages, Feb. 14, 2001.

Jerman et al., "A Miniature Fabry-Perot Interferometer with a Corrugated Silicon Diaphragm Support," Sensors and Actuators, vol. A29, No. 2, pp. 151-158, Nov. 1991.

Kurochkin et al., "Complex-Cavity Two-Mode CO2 Laser for Saturated Intracavity Absorption Spectroscopy," Optical Spectroscopy, vol. 68, No. 6, pp. 793-797, 1990.

Kurochkin et al., "Three-Mirror Cavity CO2 Laser for Intracavity Saturated-Absorption Spectroscopy," Optical Spectroscopy, vol. 65, No. 2, pp. 265-267, 1988.

O'Keefe et al., "Cavity Ring-Down Optical Spectrometer for Absorption Measurements Using Pulsed Laser Sources," Review of Scientific Instruments, 59, 11 pages, 1988.

Paul et al., "Cavity Ringdown Measures Trace Concentrations," Laser Focus World, pp. 71-80, Mar. 1997.

Richman et al., "Continuously Tunable, Single-Longitudinal-Mode, Pulsed Mid-Infrared Optical Parametric Oscillator Based on Periodically Poled Lithium Niobate," Optical Society of America, vol. 17, No. 7, pp. 1233-1239.

Sadeghi et al., "Cavity Ring Down Spectroscopy Applied to Plasma Diagnostics," Proc. Int. Symp. Laser-aided Plasma Diagnostics Lake Tahoe, CA, 8 pages, Sep. 1999.

Scherer et al., "Infrared Cavity Ringdown Laser Absorption Spectroscopy (IR-CRLAS) in Low Pressure Flames," Applied Physics B., vol. 64, pp. 699-705, 1997.

Schweber, "An Old Communications Problem Reoccurs in Optical-Communication-System Design—How it Works: Making the Laser Diode Tunable", EDN, 3 pages, Sep. 28, 2000.

Shimizu et al., "Stark Spectroscopy by 10μ Lasers Using a Multipath Cell," Journal of Applied Physics, vol. 46, No. 1, pp. 258-259, Jan. 1975.

Smirnov et al., "Dye Lasers Using a Three-Mirror Cavity with Lamp Excitation," 4 pages, 1981.

Spence et al., "A Laser-Locked Cavity Ring-Down Spectrometer Employing an Analog Detection Scheme," Review of Scientific Instruments, vol. 71, No. 2, pp. 347-353, Feb. 2000.

Sze, "Physics of Semiconductor Devices." pp. 763-765, John Wiley & Sons, N.Y., 1982.

Tayebati et al., "Microelectromechanical Tunable Filter with Stable Half Symmetric Cavity," Electronics Letters, IEE Stevanage, GB, vol, 34, No. 20, pp. 1967-1968, Oct. 1998.

Tayebati et. al., "Widely Tunable Fabry-Perot Filters Using High Index-Contrast DBRs," Design and Manufacturing of WDM Devices, Dallas, Texas, Nov. 4-5, 1997, SPIE vol. 3234, pp. 206-218, 1998.

Yang et al., "Back-Illuminated GAN/AlGAN Heterojunction Photodiodes With High Quantum Efficiency and Low Noise," Applied Physics Letters, vol. 73, No. 8, pp. 1086-1088, XP000777678, Aug. 24, 1998.

He et al., "High-Resolution Cavity Ring-Down Absorption Spectroscopy of Nitrous Oxide and Chloroform Using a Near-Infrared CW Diode Laser," Chemical Physical Letters, vol. 2, XP-002564849, pp. 527-534, 1998.

Gillis et al., "Photoacoustic Spectroscopy for Quantitation of Trace Gases in Air," Chemical Science and Technology Laboratory National Institute of Standards and Technology, Industrial and Analytical Instruments and Services Forensics and Homeland Security, 2 pages, prior to Jul. 21, 2008.

Siegman, "Lasers, Chapter 11: Laser Mirrors and Regenerative Feedback," 5 pages, 1986.

US 7,902,534 B2

CAVITY RING DOWN SYSTEM HAVING A COMMON INPUT/OUTPUT PORT

This application is a continuation-in-part of U.S. patent application Ser. No. 11/633,872, filed Dec. 4, 2006, which is a continuation-in-part of U.S. patent application Ser. No. 10/953,174, filed Sep. 28, 2004, now U.S. Pat. No. 7,145,165.

U.S. patent application Ser. No. 11/633,872, filed Dec. 4, 2006, is hereby incorporated by reference. U.S. patent application Ser. No. 10/953,174, filed Sep. 28, 2004, now U.S. Pat. No. 7,145,165, is hereby incorporated by reference.

BACKGROUND

The invention pertains to optical systems having loop-like light paths, and particularly to paths having sample fluids inserted into them. More particularly, the invention pertains to light inputs and outputs of the systems.

SUMMARY

The invention is an optical system having a loop-like light path with a common input and output port.

BRIEF DESCRIPTION OF THE DRAWING

FIG. 11 is a graph showing the signal when the low gain amplifier is on and the signal when the high gain amplifier is on;

DESCRIPTION

It is desirable for simplicity and spatial considerations to provide a signal and make the ring down measurement in a ring down system out of one mirror port. In this way, this mirror may have the lowest reflectance of the system and provide the strongest ring down signal as well as permitting the most light to go into the cavity. Typically with the input light and the detected light being measured at the same port, the reflected input light signal may swamp the weaker ring down light signal.

A detector may measure the light leaking out of the cavity through the high reflectance mirror. The reflected signal is strong and it may be used to tell when the magnitude of the stored light is greatest and optimally coupled into the cavity by the strength of the reflected signal. When the signal is minimal on the detector, a signal may be generated and provided to a switch, such as an acousto-optic (AO) modulator, to shut off the input beam to the cavity. Additionally and very slightly later, a signal may be sent to the detector amplifier circuit on the input mirror to turn on a high gain detector amplifier which would have been swamped earlier by the reflectance off of the input mirror of the reflected laser beam that was not coupled into the cavity. With this signal eliminated by the AO modulator, the cavity detector may just see the ring down signal coming out of the cavity port. The port may be situated at the lower reflectance mirror of the three mirrors. A processor connected to the detector may process and analyze the signal strength during the ring down time period and make a loss measurement. At the end of the ring down time, the light source may be turned back on and the power to the high gain amplifier turned off.

This approach may be used to maintain the largest ring down signal detection and radiation input coupling to the cavity while still not swamping the ring down detector with the input radiation.

Figure 1:
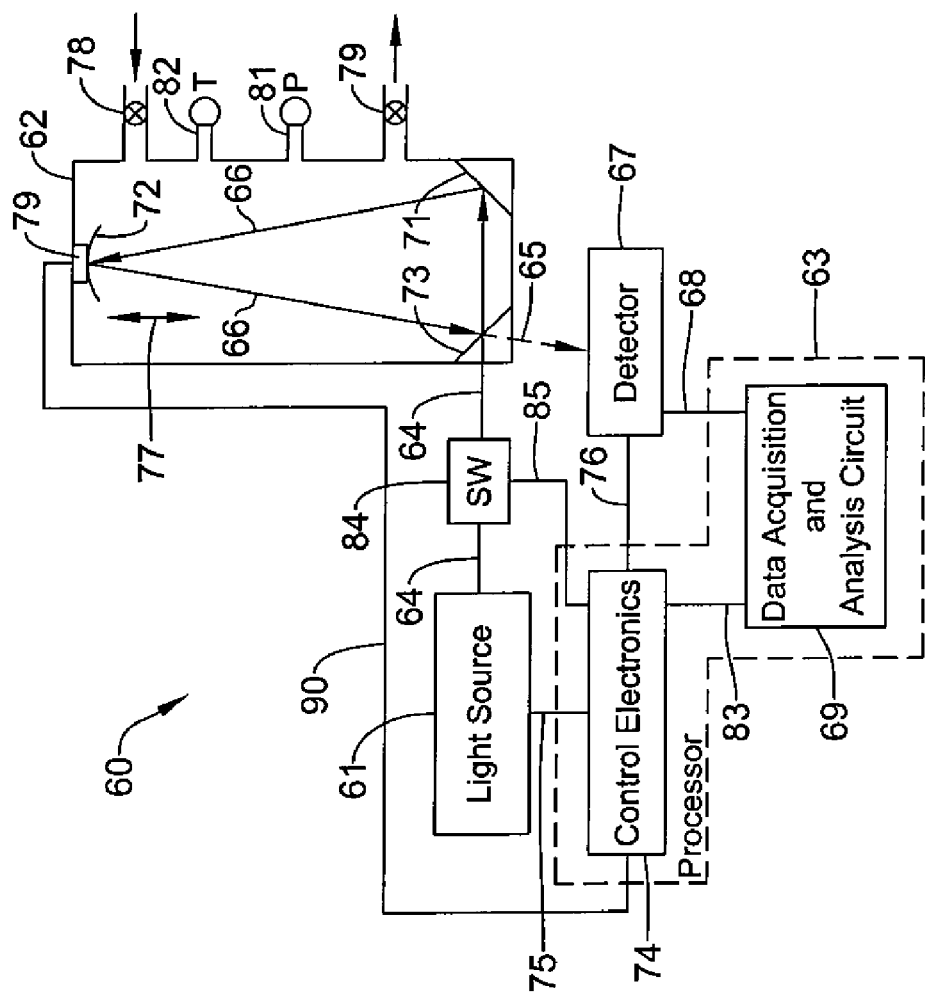
FIG. 1 is a diagram of a ring-down cavity.

As shown in FIG. 1, a light source 61 (e.g., a tunable laser) may be coupled to a three mirror optical ring-down cavity 62. One of the mirrors, e.g., mirror 72, may have a slight or significant radius curvature to improve stability so that a light beam 66 stays within the cavity. Other mirrors 71 and 73 may optionally have a curvature. Cavity 62 may be a block ring cavity or, alternatively, a ring cavity akin to a cavity of laser system though not necessarily having two lasers going through it. Cavity 62 may have two, three, four mirrors, or any other number of mirrors which can provide a light path selected from various possible routes for light in the cavity.

There may be a detector 67 and detection circuit 63 to extract the ring-down rate from an exponentially decaying ring-down waveform. A technique may be used to measure trace concentrations of gases in the near infrared region using a continuous or pulsed wave excitation 64 in a cavity-ring down spectroscopy cell or cavity 62. Cavity ring-down spectroscopy may be an absorption technique in which light 64 is coupled into the cavity 62 which may be a high finesse optical resonator. The cavity 62 may be tuned to the absorption line of the gas in the cavity being sensed and quantitatively measured. Cavity 62 may be tuned such that light 66 is in phase with the incoming light 64. This tuning, such as adjusting the path length of light 66, may be applicable to other kinds of cavities, such as those with two mirrors, four mirrors, and the like. Tuning the cavity with mirror 72 adjustment 77 with an actuator 79 may be one way of adjustment. Similarly, light source 61 may have an output wavelength tuned to the absorption line of the gas in the cavity.

By monitoring the decay rate of the light 66 inside the cavity with detection circuit 63 and detector 67, one may determine a concentration of a particular gas in the cavity 62. The near infrared or other wavelength light 65 detected from cavity 62 may contain vibrational overtone transitions and forbidden electronic transitions of various atmospheric species of gas. System 60 may obey Beer's law and provide a highly accurate concentration determination of sample gas in cavity 62. The effective path length of the light 66 in the cavity may be about a hundred or more times larger than the physical size of the cell 62 due to highly reflective dielectric mirrors 71, 72 and 73. Mirror 72 with adjustment 77 may be used for tuning the path length of cell 62 for light 66.

There may be fast trace gas impurity measurements of critical molecules such as $H_2O$, CO, $NH_3$, HF, HCl, $CH_4$ and $C_2H_2$. Such measurements may be made in seconds. Trace moisture concentration may be measured at levels from parts per billion (ppb) to parts per trillion (ppt).

Light source 61 may send a continuous wave (or possibly pulsed) light signal 64 to cell 62. Signal 64 may be regarded as a signal 66 that is reflected around in cell 62 from mirror 71, to mirror 72, to mirror 73, to mirror 71 and so on until the signal 66 diminishes. Some of the light may leave cell 62 as light 65 and impinge detector 67. Detector 67 may convert light signal 65 to an electrical signal 68 that goes to a data acquisition and analysis unit 69. Control electronics 74 may receive signals 76 and 83 from detector 67 and data acquisition and analysis unit 69, respectively, and send a control signal 75 as needed to light source laser 61. A control signal 85 may be provided to an optical switch 84 for blocking light 64 to cavity 62. Also, a control signal 90 may be sent to a moveable support 79 of mirror 72 to provide tunability of the path for light 66. Support 79 may be a piezoelectric transducer that moves mirror 72 along an axis 77 for tuning and/or modulating of the path length of cell 62.

One may detect a certain fluid using a light source 61 tuned on a transition band, near a particular frequency. Using system 62, one may be able to measure the concentration of the fluid in some medium. The certain fluid and associated medium may enter cavity 62 via a port 78 and exit the cavity via a port 79. Ports 78 and 79 may include or be valves. Port 81 may be for a connection to a pump and port 82 may be used for a gauge, or vice versa. One or more hollow optical fibers to and from the ring cavity 62 may be used to provide gas to or take gas from the ring cavity. The gas may be compartmentalized in the cavity with Brewster windows.

The system 60 may provide for an intrinsic measure of absorption. The CRDS sensitivity may equal $$(\Delta t/t) (L_{opt}/L_{cav}) (1/F_{acq})^{1/2}$$

Another relationship may be:

$$L_{opt} \sim L_{cav} / [n_{mirror}(1-R)] \sim 10^4 L_{cav}$$

Typical sensitivity of system 60 may be at about $10^{-6}$ to $10^{-10}$ cm$^{-1}$ for multimode light and about $10^{-9}$ to $10^{-12}$ cm$^{-1}$ for single mode light. System 60 may be built on the strengths of a MEMS etalon, various laser system technologies and VCSELs. The cavity 62 may be fabricated, formed or machined, or the like as a triangular or other structure from one or several pieces of solid material. Cavity 62 may be ring laser gyroscope cavity or have a structure like that of a ring laser gyroscope cavity. Light source 61 may, for example, be a tunable laser, or other kind of appropriate light source.

To reiterate, at the corners of a triangular cavity 62, there may be the mirrors 71, 72 and 73. Mirror 73 may leak some light 66 from the cavity as light 65 to detector 67 for detection and analysis purposes. For instance, mirror 73 may have a small hole for input and output for light 64 and 65, respectively. In this case, the mirror 73 may be fully reflective. Detection of light 65 may note intensity versus time, frequency, and other parameters as desired. Mirrors 71, 72 and 73 may be high or low reflectance mirrors, or be a combination of them.

The system 60 may consist of not just the external light source 61 (such as a tunable laser), but a mechanism, such as an optical switch 84, for rapidly extinguishing the incident light. A corner of the cavity light path with mirror 73 may be an input and an output port for cavity 62. The input and output may be integrated into a common optical coupler or port. The highly reflective mirrors may contain much of the light traveling around along the cavity 62 ring light path. However, some of the light may exit from the cavity through the port or mirror 73 and go directly to detector 67.

Figure 2:
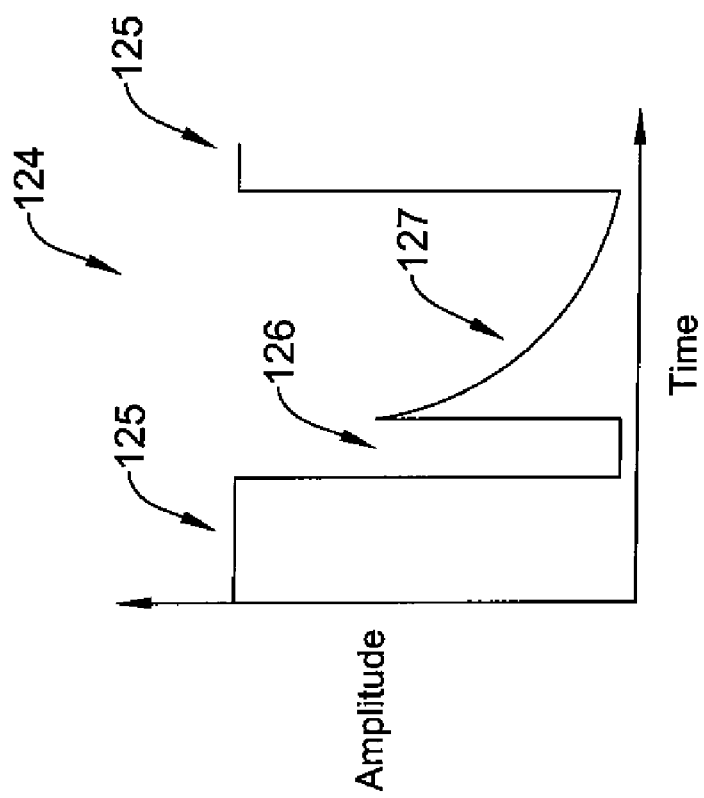
FIG. 2 is a graph of an application of the cavity of the device being utilized as a cavity ring down sensor.

FIG. 2 is a graph 124 of an application of the cavity of the device shown in some of the Figures discussed herein being utilized as a cavity ring down sensor. The graph shows amplitude versus time at the detector. For example, detector 67 of the setup shown in FIG. 1 may be a multi function detector which senses intensity of light to the cavity 62 in one function, as shown by a portion 125 of graph 124. Portion 125 may represent light provided to the cavity from the source. Another function of the of the detector 67 may include coupling to the cavity at portion 126 and measuring the light signal in the cavity at portion 127 after a supply of light to the cavity virtually ceases at the coupling portion 126 due to such things as optical switch 84. Portion 127 shows an example decay of the cavity light amplitude of the cavity ring down device 60. The amplitude and the time of the ring down may provide information about a sample fluid which may in cavity 62. Also, wavelength of the light and absorption properties of the sample may be useful. A processor (e.g., processor 63 of FIG. 1) along with other items such as tables and algorithms may aid in determining information about the sample. After a decline of signal 127, light may again be provided to the cavity a portion 125 repeat the ring down cycle.

Figure 3:
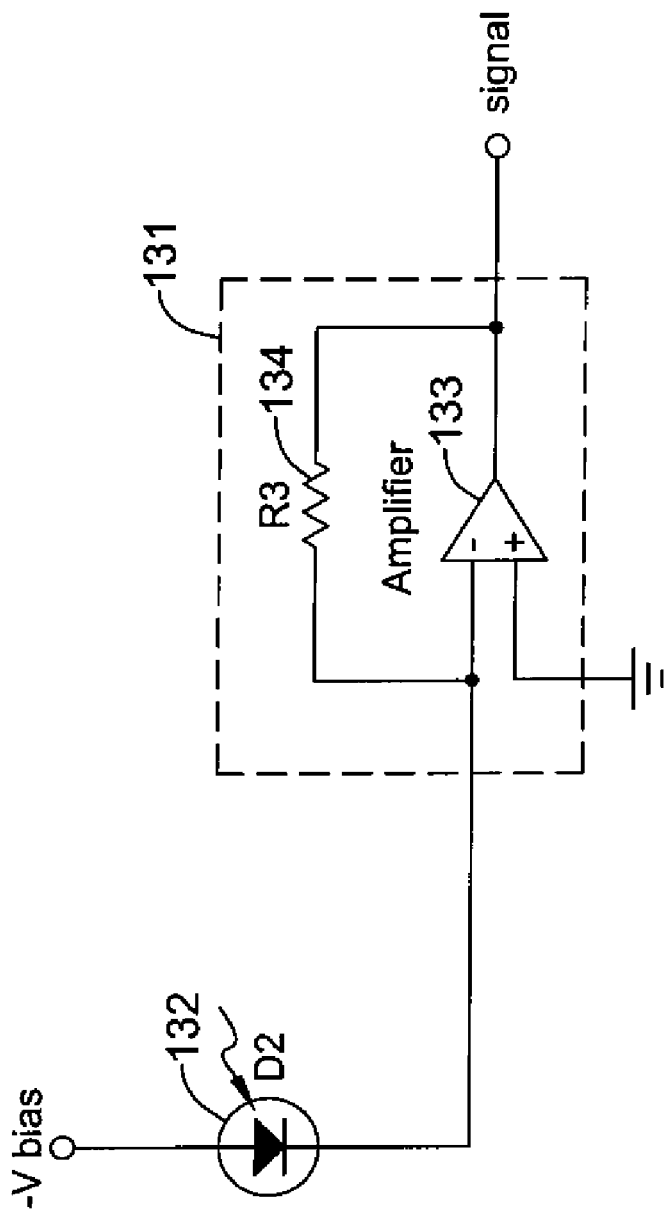
FIG. 3 is a schematic of a basic trans-impedance amplifier circuit.

FIG. 3 is a schematic of a basic trans-impedance amplifier circuit 131 commonly used in photo sensing applications such as those of detector 67. Detector 67 may incorporate circuit 131. The detector current may be converted to a voltage signal with circuit 131. There may be a photo-diode 132 having an anode connected a minus bias voltage and a cathode connected to an inverting input of an operational amplifier 133. The non-inverting input may be connected to a reference voltage or ground. The output of amplifier 133, for providing the output voltage indicating a magnitude of light impinging diode 132, may be connected to the inverting input via a gain resistor 134. The output of amplifier 133 may be included in signal 68 to processor 63.

Figure 4:
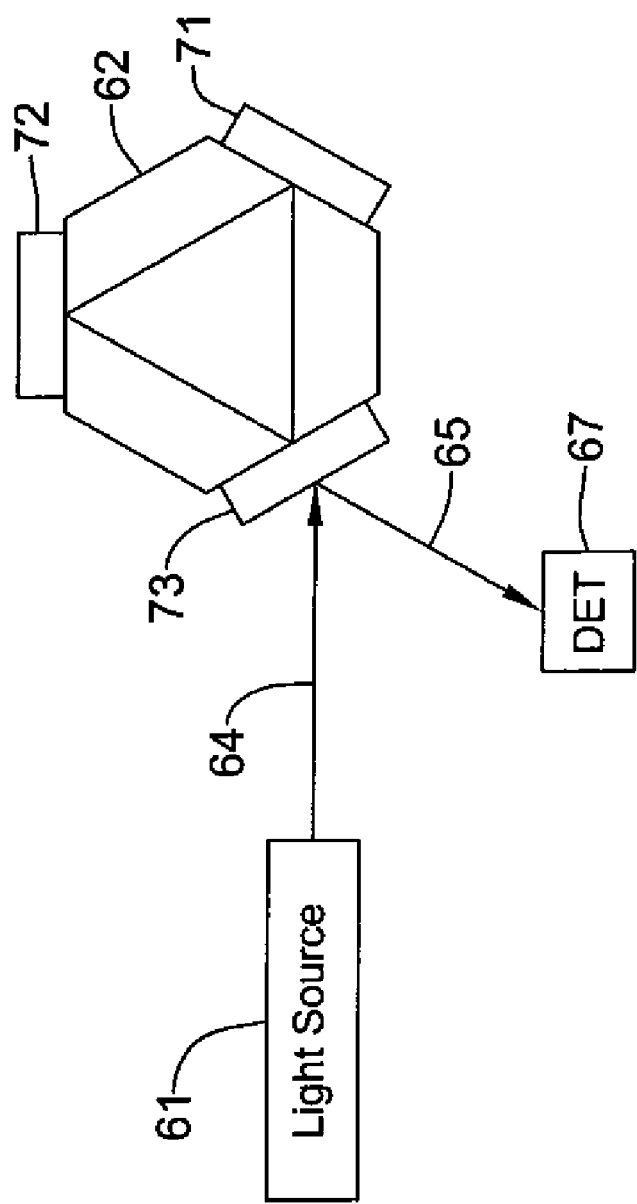
FIG. 4 is a diagram of a basic ring-down cavity having laser beam capture which results in a drop in the signal.
Figure 5:
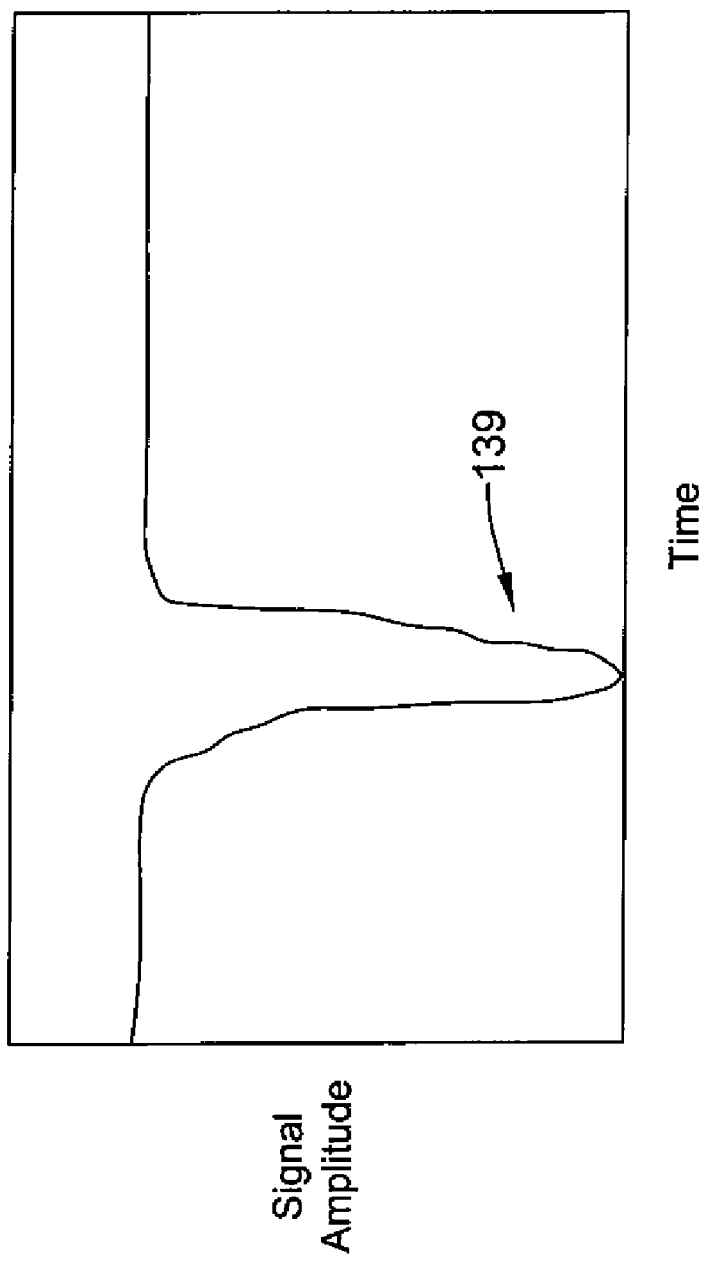
FIG. 5 is a graph of the signal of the cavity shown in FIG. 4.

The pathlength of cavity 62 of FIG. 4 may change. At some point, cavity 62 builds up power. The light coming out of cavity 62 may interfere with an input light beam 64 from light source 61 causing a drop in a signal 65 to a detector 67. If the output mirror transmission is about half of the total cavity loss, the dip 139 in light signal 65 as indicated by electrical signal 68 from detector 67, may approach zero as shown in the graph of signal amplitude versus time in FIG. 5.

Figure 6:
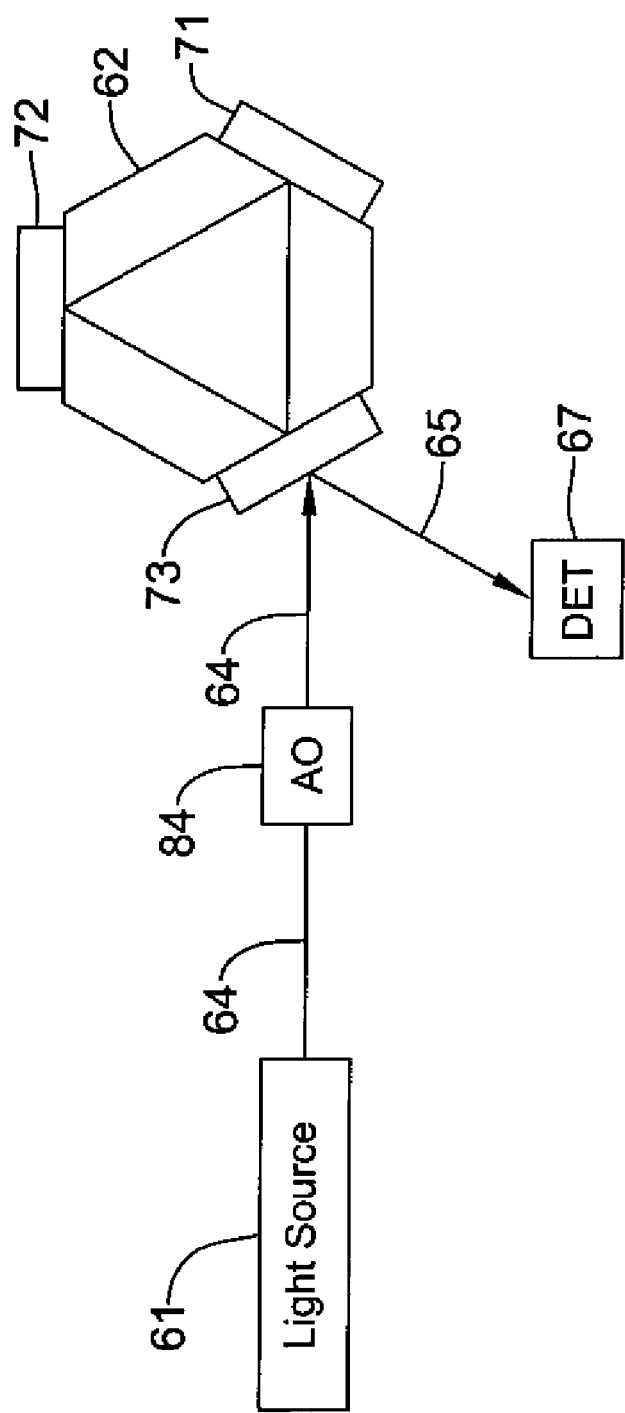
FIG. 6 is a diagram of the basic ring-down cavity having an acoustic optical switch.

If the output mirror 73 transmission is half of the total cavity 62 loss, the dip 139 in the signal, shown by either light signal 65 or its electrical representative in signal 68, can approach zero. With this situation, FIG. 6 shows the acoustic optical (AO) switch 84 between the light source 61 and cavity 62. At the bottom of the resonance curve 142, the AO cell 84 may turn off the input beam 64. From then on, just the light left in cavity 62 may be hitting the detector 67.

Figure 7:
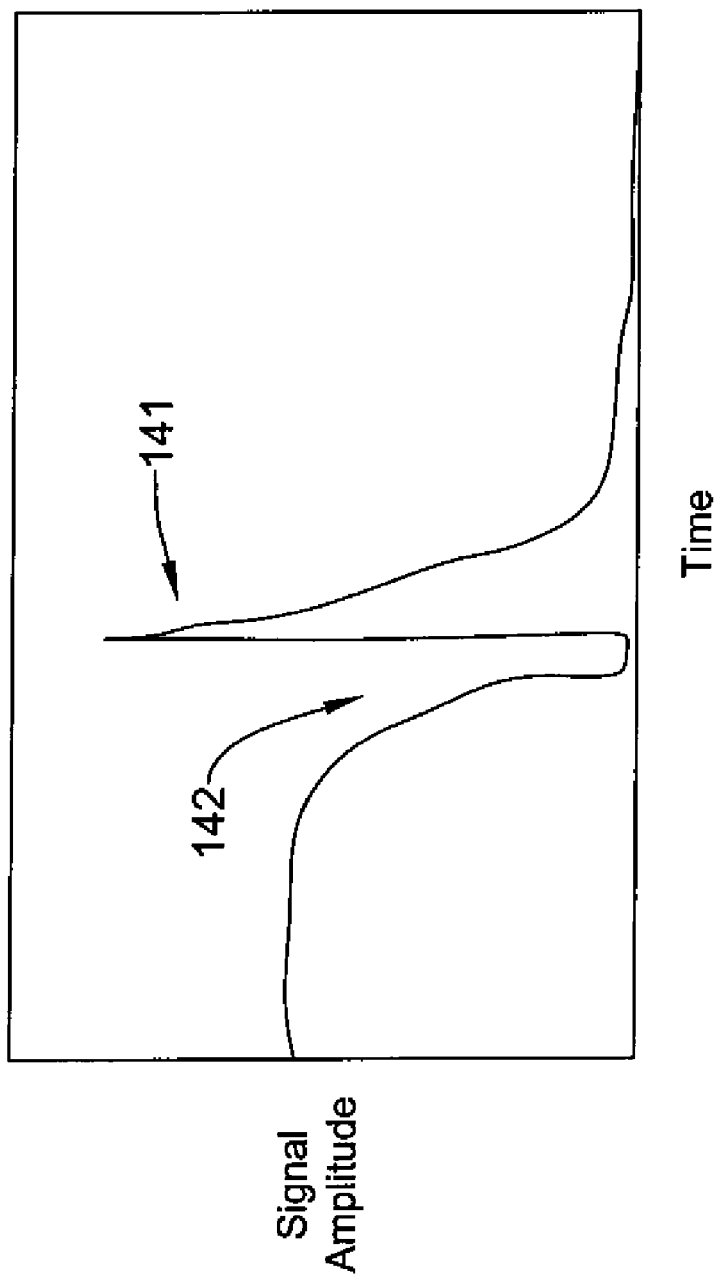
FIG. 7 is a graph of signal where the acoustic optical switch turns off the input bean to the cavity in FIG. 6.

A particular effect may be noted in FIG. 7. When the light source 61 is turned off, the start 141 of the decay can actually have a higher power level than the power level at the curve portion 142 of the light that the source 61 had before resonance.

Figure 8:
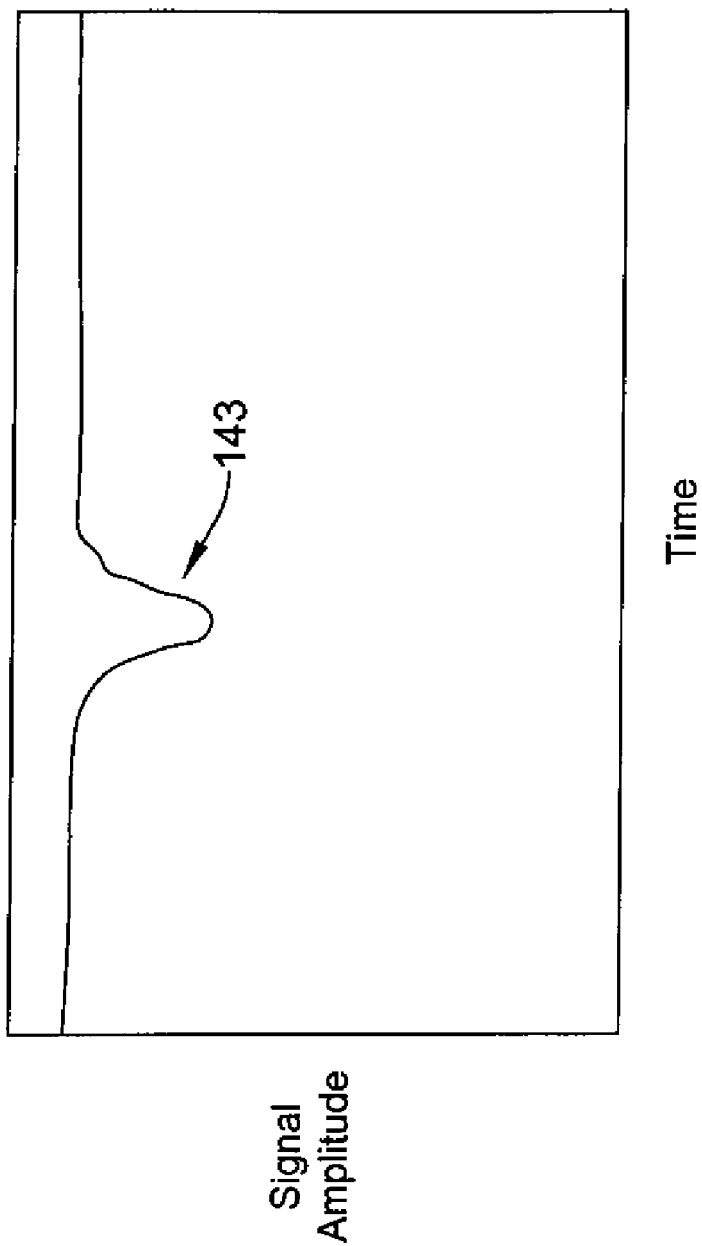
FIG. 8 is a graph of a signal in the cavity of FIG. 4 where a dip in the signal does not come down very far.
Figure 9:
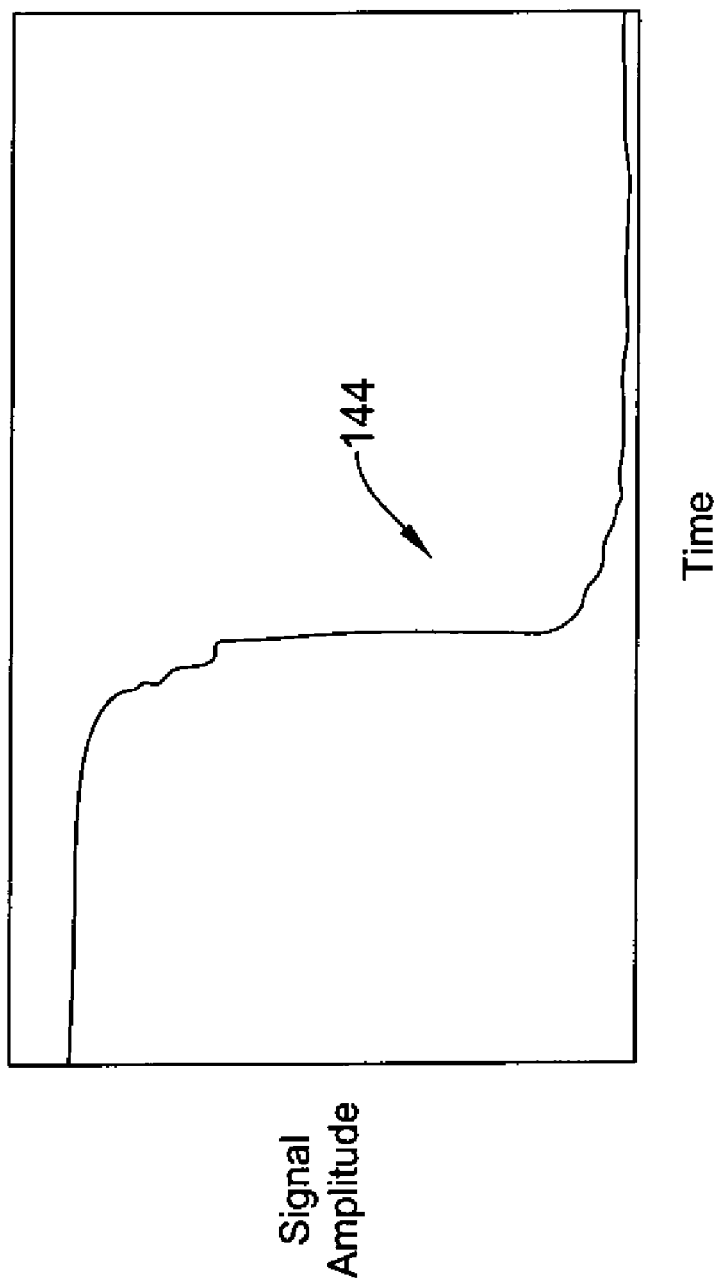
FIG. 9 is a graph of a signal in the cavity of FIG. 6 goes through a large drop when the light source is turned off.

Generally, depending on a number of factors, the dip 143 in the signal 68 might not come down very far, as shown in FIG. 8. When AO cell 84 turns off the light source 61, the detector signal 68 may go through a large drop 144, as shown in FIG. 9. Amplifier effects (internal temperature or other items) during this transient, may cause the decay signal to be distorted. Because of that, this has not necessarily been the most desirable lossmeter configuration.

Figure 10:
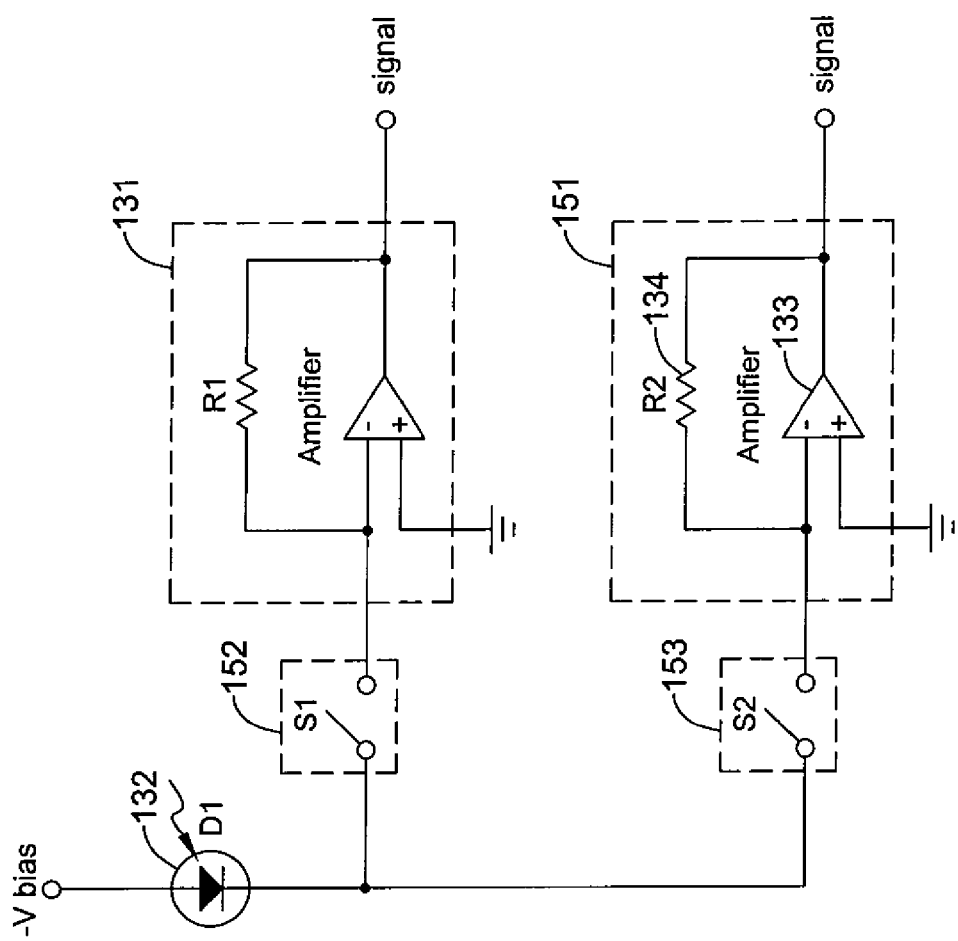
FIG. 10 is a schematic of a dual amplifier approach for providing a low gain for detecting the resonant peak and a high gain for detecting a small decay signal.
Figure 11:
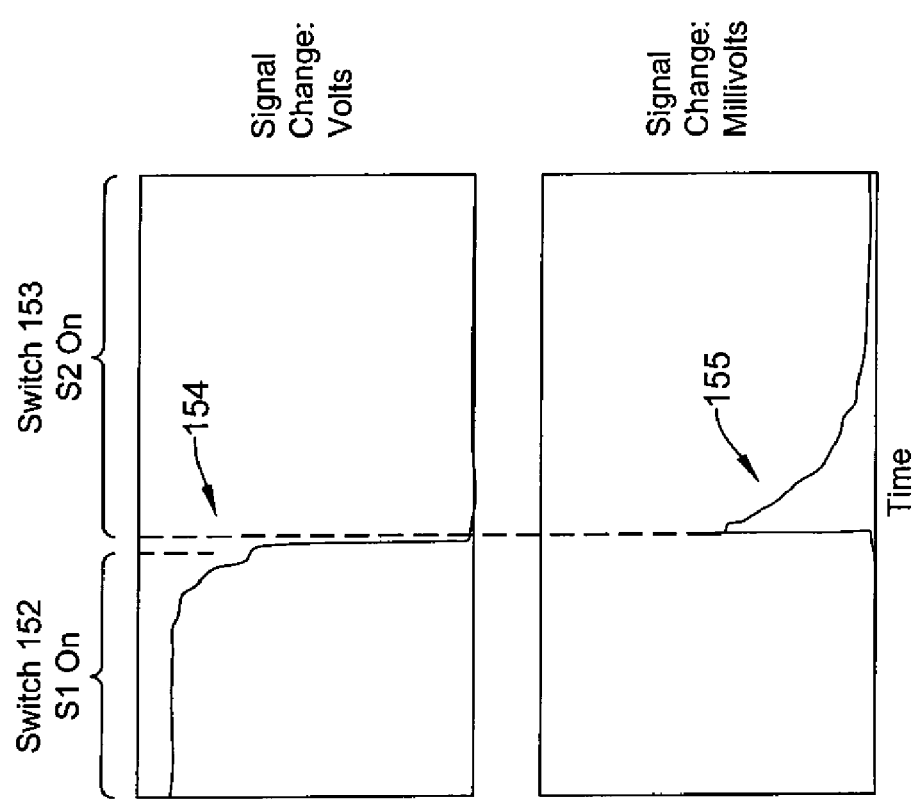

Detector 67 may have two separate amplifiers 131 and 151, as in FIG. 10. Items 152 and 153 may be high speed electronic switches. Much of the time, switch 152 may be on. Amplifier 131 may have low gain and be used to detect a resonance peak 154, as in FIG. 11. At the bottom of the resonance peak 154, the AO cell 84 may stop the light beam 64 to cavity 62.

Switch 153 may then be turned on, connecting the detector 132 current to amplifier 151. Amplifier 151 may have a higher gain (e.g., programmable gain) than amplifier 131. Since the amplifier 151 output does not have a large voltage transient, the small decay signal 155 may remain undistorted. Amplifier 131 is applicable where the signal change is in volts. Amplifier 151 is applicable where the signal change is in millivolts.

Figure 12:
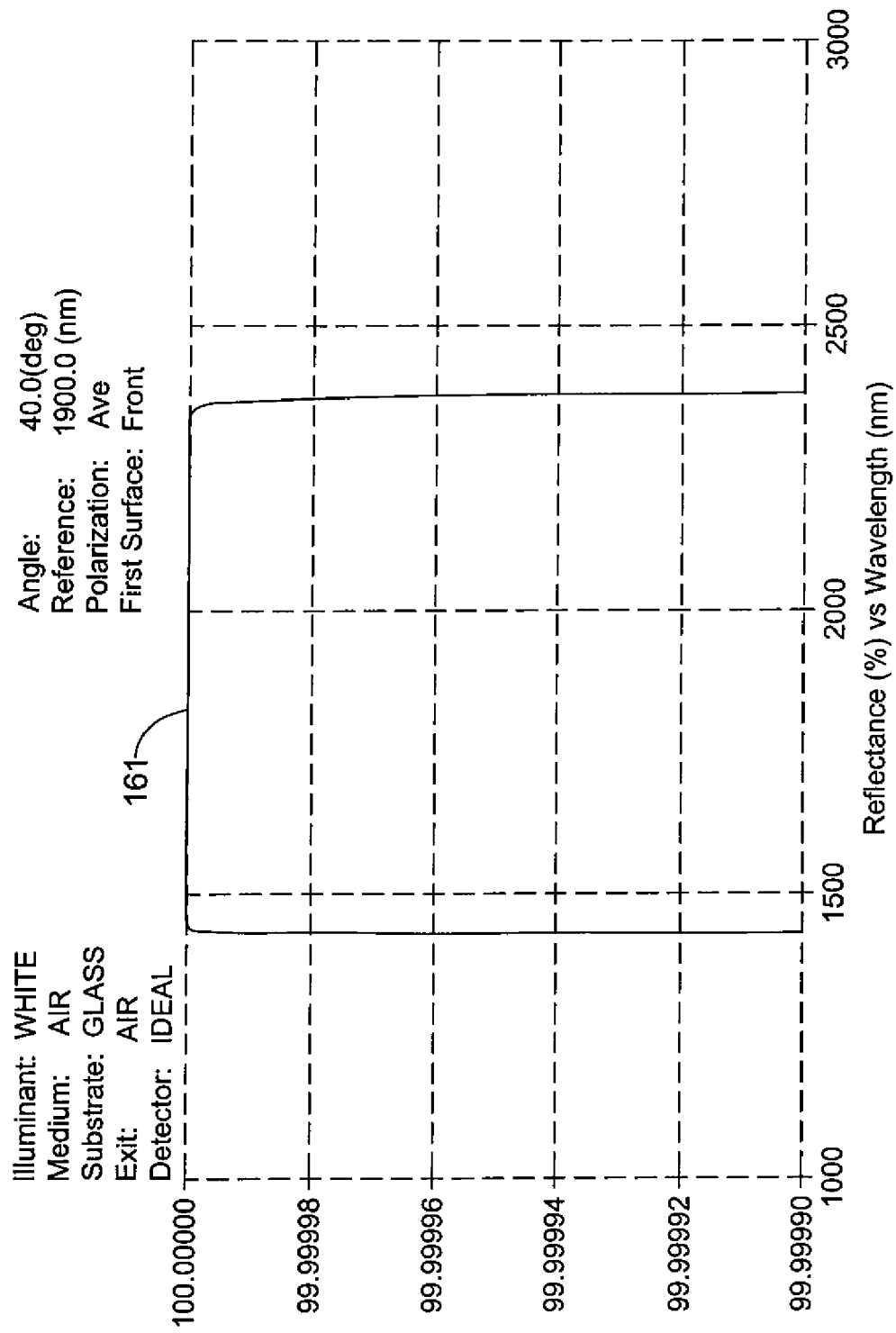
FIG. 12 is a graph of reflectance versus wavelength of a mirror having many pairs of thin films.
Figure 13:
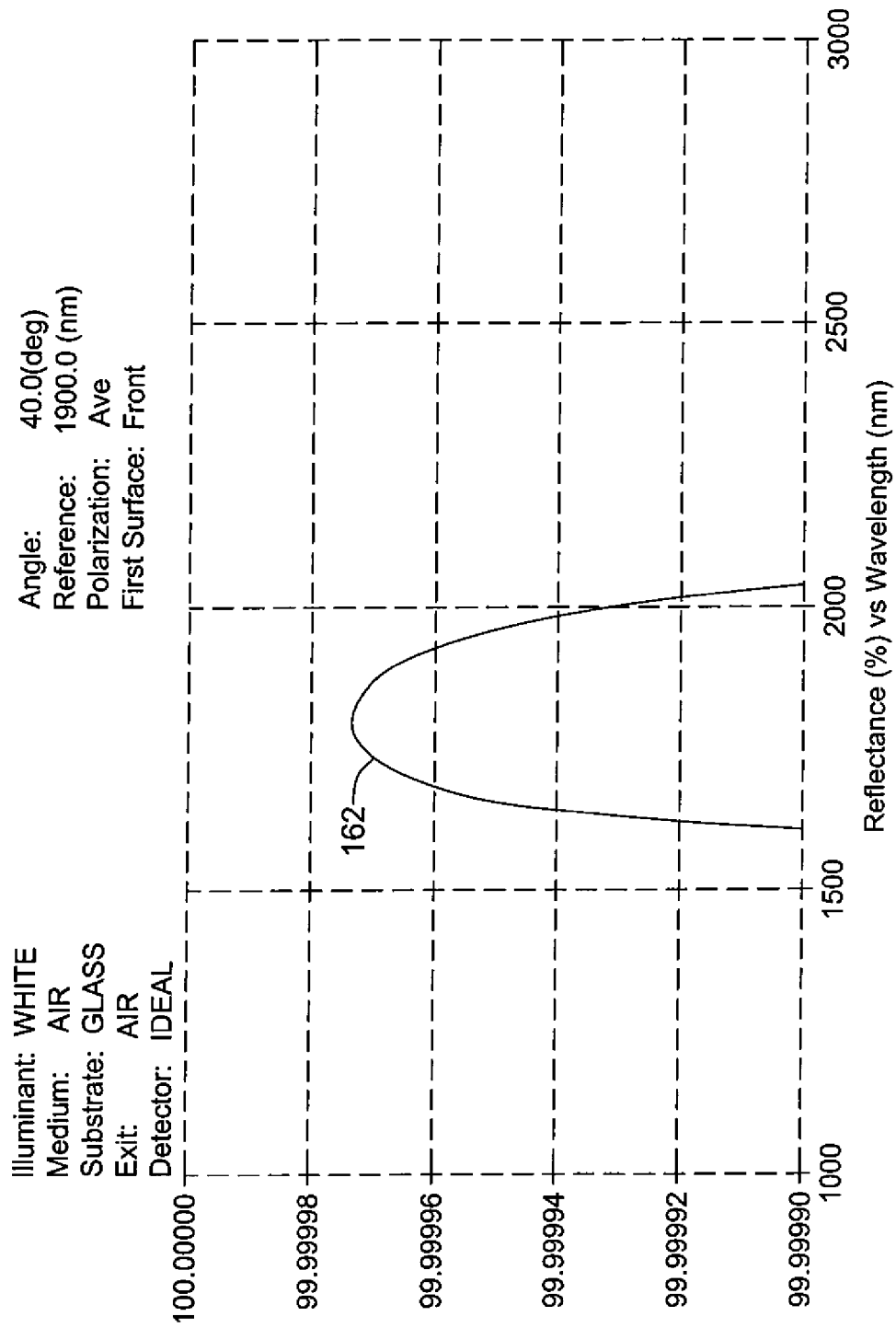
FIG. 13 is a graph of reflectance versus wavelength of a mirror having less pairs of thin film layers than the mirror in FIG. 12.

There may be a signal benefit to having one input/output mirror in the CRDS system. FIGS. 12 and 13 are graphs of gain versus reflectance of a mirror. A non-input/output mirror 71, 72 with high reflectance curve 161 may be generated by adding many (e.g., 30) extra pairs of high and low index quarter wave films of Si and $SiO_2$. The wider range of ultra high reflectance may be compared to the mirror reflectance curve 162 in FIG. 13 of another mirror. This mirror may be the same mirror as reviewed in FIG. 12 except with fewer film pairs (e.g., 8) designed to achieve a reflectance of 20 ppm (99.998%) to be used for input and output mirror 73. In a three mirror cavity, the reflectance may be a product of the reflectance of the three mirrors, and so with wide band high reflectance mirrors, the reflectance is virtually identical to the reflectance shown in the graph in FIG. 13 for the one lower reflectance mirror. In a cavity with three lower reflectance mirrors, the operating wavelength band may be approximately the same as the product of the three lower mirror reflectances, but all of the light may be leaked out of the one lower reflectance mirror giving effectively three times the "leak decay" signal intensity.

Figure 14:
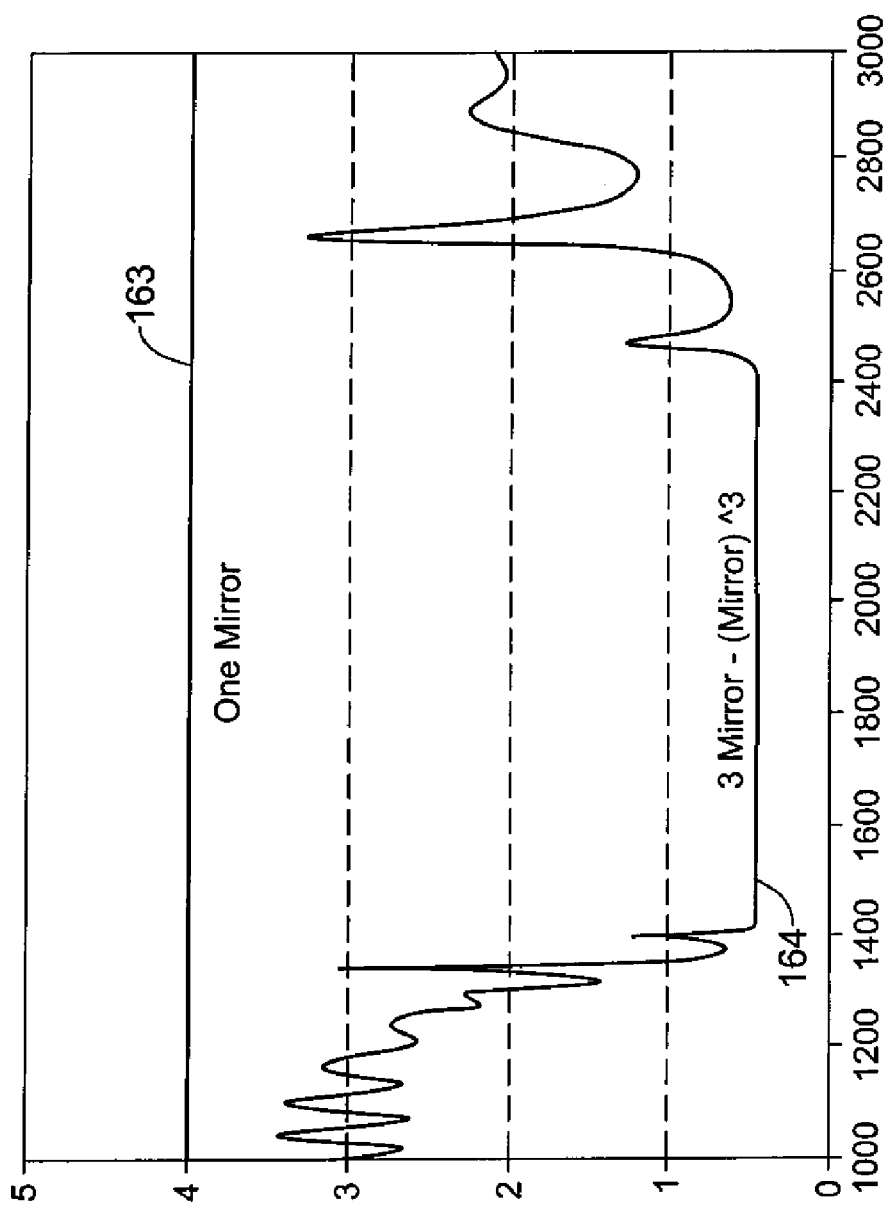
FIG. 14 is a graph showing the relative strength of a light leak with three mirrors of equal high reflectance versus two mirror of 100 percent reflectance and one mirror of high reflectance.

Since the external power is $4*T^2/Loss^2$, having one mirror with all the loss means that the relative output signal is about 4 units of magnitude, as shown by curve 163 in FIG. 14. If the loss is divided among three mirrors, then the output signal may be 4/9 or 0.44, as shown by curve 164. Thus, the single mirror dual input output mode may provide a signal for the same loss that is 11 times greater. The graph shows essentially the relative strength of an output signal with three mirrors of one high reflectance versus an output signal for two mirrors of 100 percent reflectance and one mirror of high reflectance.

Optical cavity 62 ring down signal amplitude may be noted relative to mirror transmittance considerations. The cavity may be pumped and observed through same mirror. One may pump the cavity at an optical resonance peak (assume a $TEM_{00}$ mode for simplicity). Input mirror transmittance (power) may be $T_{in}$, cavity loss may be γ (includes $T_{in}$), the input power may be taken to be one (i.e., normalize the results to $P_{in}$). At resonance the intra-cavity power may build up to $P_{cav}=4T_{in}/\gamma^2$. After this condition is established, the input beam may be shut off. The initial value of the exponentially decaying cavity power, observed exiting the cavity through the (former) input mirror, may be $P_{out0}=4T_{in}^2/\gamma^2$. As $T_{in}$ becomes all of the total loss gamma (γ), Pout may be four times the $P_{in}$ initially. For cases where Tin is 50 percent of the total cavity loss, the $P_{out}$ may be equal to the $P_{in}$ initially. For values where $T_{in}$ is less than 50 percent of the total loss, $P_{out}$ may be less than the $P_{in}$ initially.

Figure 15:
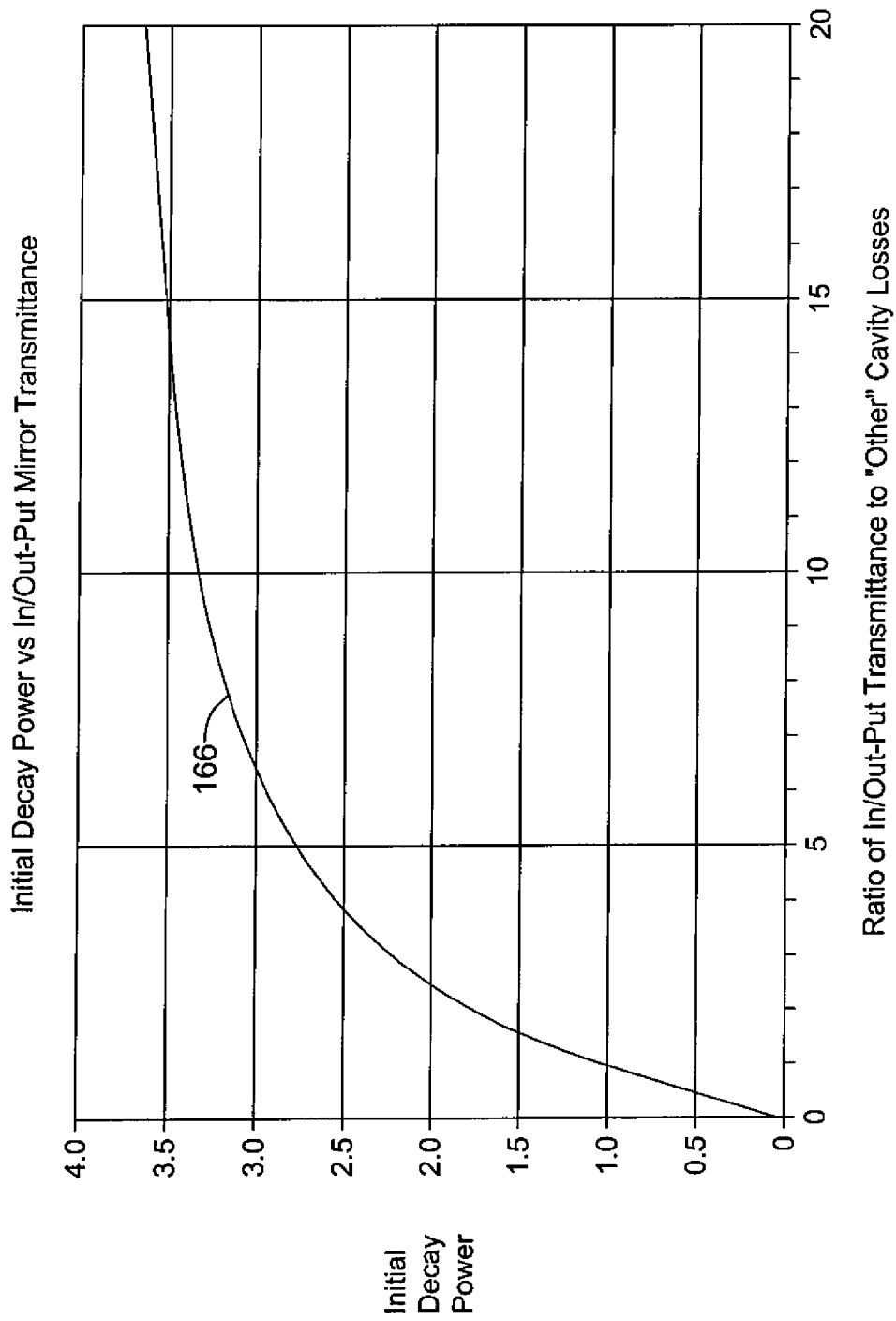
FIG. 15 is a graph of initial decay power of a cavity versus in/out-put mirror transmittance.

The decay initial power to show the effect of "other" cavity losses, which include scatter, mirror absorption, transmittance of the mirrors other than the in/out mirror, and sample absorption, may be written as $P_{out0}=4T_{in}^2/(T_{in}+\gamma_{other})^2$. From this expression, it may be seen that, as a function of $T_{in}$, the decay initial power is a monotonically increasing function of $T_{in}$ and is greater than 1 for $T_{in}>\gamma_{other}$. Curve 166 of the graph in FIG. 15 shows initial decay versus a ratio of in/out-put transmittance to "other" cavity losses.

In the present specification, some of the matter may be of a hypothetical or prophetic nature although stated in another manner or tense.

Although the invention has been described with respect to at least one illustrative example, many variations and modifications will become apparent to those skilled in the art upon reading the present specification. It is therefore the intention that the appended claims be interpreted as broadly as possible in view of the prior art to include all such variations and modifications.

What is claimed is:

1. A cavity ring down system comprising:
a cavity; and
at least two mirrors situated in the cavity for reflecting light from one mirror to another in a ring-down manner; and
wherein a first mirror of the at least two mirrors permits light to enter the cavity, and to exit the cavity for detection.

2. The system of claim 1, comprising:
a detector proximate to the first mirror; and
an amplifier connected to the detector; and
wherein the amplifier is for amplifying signals from the detector; and
the signals are indicative of light from the first mirror.

3. The system of claim 2, further comprising a light valve which is switched on to permit light to go through the valve to the first mirror or is switched off to prevent light from going through the valve to the first mirror.

4. The system of claim 3, wherein:
the amplifier is switched on at a time when the light valve is switched off; and
the amplifier is switched off when the light valve is switched on.

5. The system of claim 4, wherein the light valve is an acousto-optic modulator.

6. The system of claim 3, wherein the amplifier has a low gain mode and a high gain mode.

7. The system of claim 6, wherein:
the amplifier is in a low gain mode at a time when the light valve is switched on; and
the amplifier is in a high gain mode at a time when the light valve is switched off.

8. The system of claim 7, wherein the amplifier comprises:
a first amplifier for the low gain mode; and
a second amplifier for the high gain mode.

9. A method for cavity ring-down measurement comprising:
inputting light through a first mirror of a cavity having at least two mirrors for reflecting light from one mirror to another in a ring-down manner; and
measuring light leaking out of the cavity through the first mirror.

10. The method of claim 9, wherein inputting the light through the first mirror does not occur while measuring the light leaking out of the cavity through the first mirror.

11. The method of claim 9, wherein:
measuring the light is accomplished with a detector and an amplifier connected to the detector;
the amplifier is off during the inputting light through the first mirror;
the amplifier is on at a time when light is not inputted through the first mirror.

12. The method of claim 9 wherein:
measuring the light is accomplished with a detector and a multiple-gain amplifier connected to the detector;
the amplifier has a low gain during the inputting of light through the first mirror;
the amplifier has a high gain at a time when not inputting light through the first mirror.

13. The method of claim 12, wherein the inputting and not inputting light through the first mirror is effected with a light valve situated between a light source and the first mirror.

14. A sensor system comprising:
a cavity;
at least two mirrors situated in the cavity for reflecting light to one another;
a source for providing light into the cavity through a first mirror of the at least two mirrors; and
a detector for detecting light from the cavity through the first mirror.

15. The system of claim 14, further comprising a mechanism for controlling an amount of light from the source to the first mirror.

16. The system of claim 15, further comprising an amplifier connected to the detector.

17. The system of claim 16, wherein the amplifier has a selectable gain.

18. The system of claim 16, wherein the mechanism for controlling an amount of light from the source to the first mirror can prevent virtually any light from going to the first mirror.

19. The system of claim 18, wherein the mechanism for controlling an amount of light from the source to the first mirror is an acoustic-optic light modulator.

20. The system of claim 18, further comprising:
a controller connected to the amplifier and the mechanism for controlling an amount of light from the source to the first mirror; and
wherein:
the controller selects a high gain of the amplifier at a time when virtually no light is going to the first mirror; and
the controller selects a low gain of the amplifier when light is going to the first mirror.

* * * * *